United States Patent [19]
Hagans et al.

[11] Patent Number: 5,550,636
[45] Date of Patent: Aug. 27, 1996

[54] SELF-TUNING METHOD FOR MONITORING THE DENSITY OF A GAS VAPOR COMPONENT USING A TUNABLE LASER

[75] Inventors: Karla Hagans; Leon Berzins; Joseph Galkowski, all of Livermore; Rita Seng, Tracy, all of Calif.

[73] Assignee: The United States of America as represented by the United States Department of Energy, Washington, D.C.

[21] Appl. No.: 425,681

[22] Filed: Apr. 18, 1995

Related U.S. Application Data

[63] Continuation of Ser. No. 117,404, Sep. 3, 1993.

[51] Int. Cl.[6] ................................................. G01N 21/00
[52] U.S. Cl. ................................................................. 356/437
[58] Field of Search ..................................... 356/432, 435, 356/436, 437

[56] References Cited

U.S. PATENT DOCUMENTS

| | | | |
|---|---|---|---|
| 4,471,220 | 9/1984 | Perry et al. | 356/51 |
| 4,990,780 | 2/1991 | Lee et al. | 250/343 |
| 5,153,672 | 10/1992 | Globig et al. | 356/436 |
| 5,173,749 | 12/1992 | Tell et al. | 350/433 |

OTHER PUBLICATIONS

Reid et al "High Sensitivity Pollution Detection Employing Tunable Diode Lasers" *Applied Optics* vol. 17, No. 2 (15 Jan. 1978).

Paper, Lawrence Livermore National Laboratory, Joe Galkowski & Karla Hagans, "Laser Absorption Spectroscopy System for Vaporization Process Characterization and Control" Sep. 1993.

Paper, Lawrence Livermore National Laboratory, Karla Hagans & Joe Galkowski, "The Use of Laser Diodes for Control of Uranium Vaporization Rates" Sep. 1993.

Paper, Lawrence Livermore National Lboratory, Leon V. Bervins, "Using Laser Absorption Spectroscopy to Monitor Composition and Physical Properties of Metal Vapors" Sep. 1993.

*Primary Examiner*—Richard A. Rosenberger
*Attorney, Agent, or Firm*—Miguel A. Valdes; William C. Daubenspeck; William R. Moser

[57] ABSTRACT

The present invention relates to a vapor density monitor and laser atomic absorption spectroscopy method for highly accurate, continuous monitoring of vapor densities, composition, flow velocity, internal and kinetic temperatures and constituent distributions. The vapor density monitor employs a diode laser, preferably of an external cavity design. By using a diode laser, the vapor density monitor is significantly less expensive and more reliable than prior art vapor density monitoring devices. In addition, the compact size of diode lasers enables the vapor density monitor to be portable.

According to the method of the present invention, the density of a component of a gas vapor is calculated by tuning the diode laser to a frequency at which the amount of light absorbed by the component is at a minimum or a maximum within about 50 MHz of that frequency. Laser light from the diode laser is then transmitted at the determined frequency across a predetermined pathlength of the gas vapor. By comparing the amount of light transmitted by the diode laser to the amount of light transmitted after the laser light passes through the gas vapor, the density of the component can be determined using Beer's law.

2 Claims, 5 Drawing Sheets

SELF-TUNING METHOD FOR MONITORING THE DENSITY OF A GAS VAPOR COMPONENT USING A TUNABLE LASER

The U.S. Government has rights to this invention pursuant to Contract No. W-7405-ENG-48 between the U.S. Department of Energy and the University of California, for the operation of the Lawrence Livermore National Laboratory.

This is a Continuation of application Ser. No. 08/117,404 filed Sep. 3, 1993.

TECHNICAL FIELD

The present invention is generally directed to a laser atomic absorption spectrometer. More specifically, the present invention relates to a diode laser atomic absorption spectrometer capable of real time vapor density calculations.

BACKGROUND OF THE INVENTION

There are numerous applications for which an economical and efficient device and method for continuously monitoring vapor densities, composition, flow velocity, internal and kinetic temperatures and constituent distributions is needed.

One such application is the Atomic Vapor Laser Isotope Separation (AVLIS) process. In the AVLIS process, uranium is vaporized and the $U^{235}$ isotope is selectively photoionized for subsequent electrostatic collection. This process is shown schematically in FIG. 1. A high power electron beam system is used to co-vaporize a mixture of uranium and iron. The economics of the AVLIS process is governed by the vaporization rate, the distribution of internal states of uranium, the collection efficiency and the component lifetime. Each of these factors are critically dependent on the specific properties of the vapor. The vaporization rate and internal temperature are directly measurable, while the collection efficiency is dependent on the flow velocity and flow circulation as well as the flux distribution. Likewise, the component lifetime in a corrosive liquid uranium environment depends on the component temperature. By vaporizing a mixture of uranium and iron, an eutectic alloy is formed having a lower melting temperature. This enables a lower operating temperature which, in turn, is more economical. The temperature necessary to maintain liquid flow on each component depends on the ratio of iron to uranium on that component. Thus, in order to optimize the AVLIS process, it is necessary to closely control the composition of the uranium-iron vapor.

Electron beam vaporization processes also represent an area of technology that would greatly benefit from a process enabling the continuous monitoring of vapor properties. One application of electron beam vaporization that would benefit from improved vapor monitoring technology is rapid prototyping with an electron beam vaporizer. Numerous alloys are comprised of elements with vastly different vapor pressures. For example, the vapor pressures of iron and molybdenum for 316 stainless steel differ by more than three orders of magnitude at 3000° K. As a result of this large vapor pressure difference, compositional variation is common. A significant need exists for a device and method capable of closely regulating the composition of the metal vapor.

The formation of titanium alloys for aerospace parts is another technology where closer regulation of vapor composition is needed. D. Hughs, *Aviation Week and Space Technology* (1991) p. 358. In the absence of a means for continuously monitoring the vapor phase, the aerospace industry currently must rely on empirical recipes to produce titanium alloys for aerospace parts. However, the rejection rate for aerospace alloys formed using empirical recipes presently exceeds 10%. By continuously monitoring the metal composition of the vapor forming the alloy, it should be possible to better control the resulting alloy composition and reduce the current rejection rate.

A simple method for continuously monitoring the presence and density of a particular component of a gas vapor could also be used to effectively monitor compliance with environmental regulations including in situ trace gas detection, waste stream analysis, atmospheric measurements and vehicle emissions monitoring. Additional applications for an improved method and device for monitoring vapor composition and properties include but are not limited to plasma etching of semiconductors, thin film deposition control and molecular beam and atomic layer epitaxy.

Several methods presently exist for determining the density of a particular component of a gas vapor. However, these methods are generally expensive, intrusive and lack the necessary accuracy, reliability and durability. For example, direct deposition sensors have been used to measure the total vapor flux onto a surface, independent of chemical composition. These sensors are commonly used for inferring the thickness of a deposited film. Examples of direct deposition sensors include load cells, quartz crystal micro-balances and chopped ion gauges.

Direct deposition sensors operate based on direct deposition of the component being measured on to the sensor and thus must be placed within the gas sample. These sensors are not able to distinguish between different deposited components and thus cannot be used to detect the density of individual components in a co-vaporization process. Further, because direct deposition sensors are intrusive, these sensors must be able to withstand extreme temperatures, often in excess of (1000° C.) and can disrupt the vapor plume of the process being monitored. In addition, because these sensors are exposed to extreme temperatures and operate by direct deposition of the component being measured onto the sensor, direct deposition sensors generally have short operating lifetimes. For example, quartz crystal micro-balance sensors generally do not have operating lifetimes in excess of 5 hours for high vaporization rate processes.

Emission spectroscopy has also been used to monitor the density of particular components of a gas vapor. Examples of emission spectroscopy systems include electron impact emission and x-ray spectrometers. Emission spectroscopy has relatively poor spectral resolution (>10 GHz) which makes it difficult to resolve similar components. In addition, emission spectroscopy requires the use of a vapor heating source which adversely affects vapor properties. Further, the diagnostic probe is necessarily subjected to the harsh environment internal to the vaporizer vessel, thereby reducing the lifetime and reliability of the diagnostic.

Atomic absorption spectroscopy has also been used to monitor the density of particular components in gas vapor samples. Atomic absorption spectroscopy has the advantage of being species specific. However, the usefulness of atomic absorption spectroscopy is largely limited by the quality of the light source. Examples of atomic absorption spectroscopy include spectral lamp and ring-dye laser based systems.

Spectral lamps are inherently low light level, broad-band, incoherent sources. As a result, in order to gather enough photons to make a density measurement, short pathlengths are necessary. Therefore, it is generally necessary to place the launch optics within the gas sample being tested. This greatly reduces the reliability and durability of spectral lamp components since they are often exposed to high temperature gas samples. In addition, the intrusive nature of spectral lamp atomic absorption spectroscopy can disrupt the vapor plume.

Spectral lamps also require recalibration any time an operating parameter or diagnostic location is altered. The need to continuously recalibrate spectral lamps arises from the fact that the emission band of spectral lamps is broad (1 GHz) and untunable. The monochromators that are likely to be used to measure vapor compositions have a broad frequency acceptance window. As a result, a narrow spectral absorption feature will have little effect on the output signal since the majority of the light transmitted from the hollow cathode will not be affected. Vapor sources that have a doppler broadened width close to that of the hollow cathode are therefore difficult to measure. The sensitivity of the photo-multiplier to significant absorption of light in the tails of the hollow cathode emission curve is much smaller than at the center of the emission curve.

Ring dye lasers have also been used in atomic absorption spectroscopy. Ring dye lasers are advantageous over spectral lamps in atomic absorption spectroscopy in several respects. Ring dye lasers provide high level coherent light. As a result, ring dye lasers enable longer pathlengths and can thus generally be employed nonintrusively. In addition, ring dye lasers enable significantly enhanced spectral resolution (1 MHz) thus enabling element specific and, in some cases, isotope specific detection. In addition, ring dye lasers are tunable over a broad wavelength range to 60 nm. In view of these advantages, ring dye laser atom absorption spectrometry is a standard technique used in the laboratory for element and isotope specific identification and quantitative measurement.

Despite its prevalent use, ring dye laser based atomic absorption spectrometry has several significant disadvantages. Ring dye lasers are very expensive, costing around $160,000 with an operating cost of around $15,000 per 1000 hours to replace the laser ion tube. Further, weekly maintenance of the ring dye laser atomic absorption spectrometer is required. In addition to being costly to operate, atomic ring dye laser atomic absorption spectrometers are large and thus are not generally portable. An additional disadvantage of ring dye laser systems is the handling and disposal of mutagenic and carcinogenic dyes as well as flammable solvents. Ring dye lasers also require a special power supply (480 V 3 phase) and water cooling.

In view of the disadvantages associated with these prior art devices, the need still exists for a simple, accurate and economical device for evaluating the density of a particular component in a gas vapor sample. All of the disadvantages noted in these prior art devices have been overcome by the Diode Laser Vapor Density Monitor of the present invention.

SUMMARY OF THE INVENTION

The present invention relates to a vapor density monitor and laser atomic absorption spectroscopy method for highly accurate, continuous monitoring of vapor densities, composition, flow velocity, internal and kinetic temperatures and constituent distributions. The vapor density monitor employs a diode laser, preferably of an external cavity design. By using a diode laser, the vapor density monitor is significantly less expensive and more reliable than prior art vapor density monitoring devices. In addition, the compact size of diode lasers enables the vapor density monitor to be portable.

According to the method of the present invention, the density of a component of a gas vapor is calculated by tuning the diode laser to a frequency at which the amount of light absorbed by the component is at a minimum or a maximum within about 50 MHz of that frequency. Laser light from the diode laser is then transmitted at the determined frequency across a predetermined pathlength of the gas vapor. By comparing the amount of light transmitted by the diode laser to the amount of light transmitted after the laser light passes through the gas vapor, the density of the component can be determined using Beer's law.

BRIEF DESCRIPTION OF THE DRAWINGS

FIG. 7 depicts the change in iron and uranium vapor density observed when a charge of iron is introduced into a pool of molten iron-uranium alloy.

DETAILED DESCRIPTION OF THE PREFERRED EMBODIMENT

Figure 1:
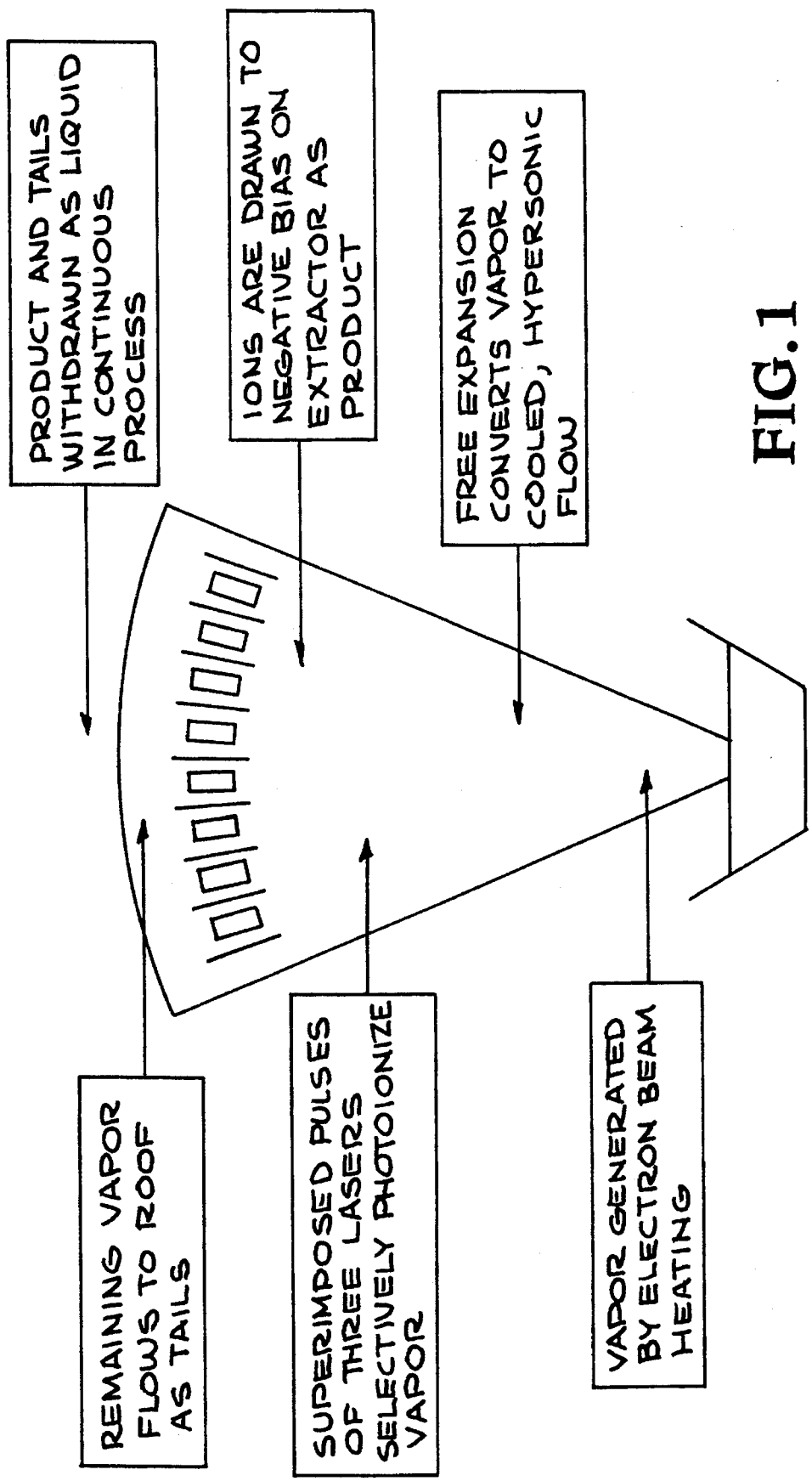
FIG. 1 provides a schematic depiction of the AVLIS process wherein uranium is vaporized and the $U^{235}$ isotope is selectively photo-ionized for subsequent electrostatic collection.

The present invention relates to a diode laser vapor density monitor and method of using the monitor for continuously monitoring vapor densities, composition, flow velocity, internal and kinetic temperatures and constituent distributions.

The diode laser vapor density monitor is a laser atomic absorption spectrometer as is the ring dye laser atomic absorption spectrometer described above. As such, the diode laser vapor density monitor enables species specific, accurate and nonintrusive real-time monitoring of a chemical species in a gas vapor sample. However, the diode laser vapor density monitor provides several significant advantages over the ring dye laser based system. Diode lasers are significantly less expensive and more reliable than ring dye lasers. In addition, there are significantly lower maintenance costs associated with diode lasers. Furthermore, diode lasers are significantly smaller than ring dye lasers and thus enable the vapor density monitor to be portable.

It is preferred that the diode laser have an external cavity design. External cavity diode lasers enable continuously tunable operation and great improvement in wavelength stability.

In addition, A 300 MHz Fabry-Perot provides periodic calibration of the length of the frequency sweep. An optogalvanic cell is used to generate the electrical equivalent of a stationary vapor source. Analysis using the optogalvanic cell with the Fabry-Perot provides an absolute frequency base with an accuracy of better than 30 MHz. The absolute frequency scale can then be used to obtain spatial information regarding the vapor plume from the absorption waveforms.

The diode laser is capable of being scanned in frequency rates of up to around 30 Hz while a ring dye system is only capable of rates of about 10 Hz. In addition, a diode laser facilitates continuous operation because there is no dye to change and the overall reliability is orders of magnitude higher. The reliability of the diode laser will also allow the elimination of several costly components. Chief among these is the wavemeter. Others include the acousto-optic modulator and the Fabry-Perot. Elimination of the wavemeter and Fabry-Perot would be possible once that diode laser has been characterized. The acousto-optic modulator is replaced by current modulating the diode to produce an intensity variation.

Vapor densities are calculated using Beer's law. Beer's law provides that the ratio of transmitted light intensity to incident light intensity $I/I_0$ is a function of the density of the sample n, the wavelength absorption cross section $\sigma$ and the pathlength of the sample 1.
Beer's Law $$I/I_0 = e^{-n\sigma l}$$

Thus, using Beer's law, one is able to calculate the vapor density n of a gas component if one knows the percentage of light absorbed T, the wavelength absorption cross section $\sigma$ and the pathlength 1 of the sample.

$$n = \frac{-\ln(T)}{\sigma l}$$

According to the present invention, one is able to precisely measure the vapor density of a component since both the percentage of light absorbed and the pathlength through the vapor can be accurately measured. The transition cross section is known and thus need not be calculated.

A diode laser emits light at a specific, selected frequency which is then passed through the gas sample to be analyzed. Prior to reaching the gas sample, a portion of the light is split off and input into a reference detector. The remainder of the light passes through the gas sample and is measured by the signal detector. By modulating the light intensity with an acousto-optic modulator or by the diode current signal, the data from the signal and reference detectors can be synchronously detected via lock-in amplifiers which serve to reduce background noise. Taking the ratio of the signal to the reference minimizes the effects of uncontrolled laser intensity variations and spurious background noise.

The frequency range of laser light emitted is selected based on the absorbance characteristics of all of the gas components that may be present in the gas sample being analyzed. All atoms and molecules have their own characteristic light absorption patterns, these patterns being defined by their atomic transition cross sections at the various frequencies measured. In order to insure that only the absorbance of the gas component of interest is being measured, it is important to select a frequency at which no other gas components absorb light.

The diode laser is operated in two different modes, typically interleaved. In the standard configuration, the frequency of the diode laser is periodically swept to cover the total absorption waveform. The advantage of this waveform is that no calibration is required once the pathlength and cross section are specified. In the high speed configuration, the diode laser is locked to the center of the absorption waveform. The ratio of the signal to the reference and the scaling of this ratio is controlled by other components of the vapor density monitor, thereby allowing the monitor to provide an almost continuous measure of the vapor density and other calculable properties. The high speed configuration is calibrated by periodically operating the laser in the standard configuration to correct for changes in the baseline due to coating of the viewpoints, changes in the background noise, as well as changes in the absorption waveform due to physical changes in the vapor plume.

The shape of the absorption waveform for a particular transition is process and geometry specific. Therefore, in order to insure accurate and reproducible density measurements, it is essential to accurately determine the particular frequency at which absorption is being measured.

The method of the present invention insures that absorption is repeatedly measured at the same frequency by tuning the laser to either a local absorption minimum or maximum within a narrow frequency range, generally 50 MHz. This is accomplished by sweeping the frequency output of the diode laser through a narrow frequency range by changing the cavity length of the diode laser. Since the absorption pattern of a particular gas component does not vary between samples, measurement of absorbance at a local maximum or minimum within a known narrow frequency range insures that all measurements are conducted at the same frequency. Further, by measuring absorbance at a local maximum or minimum, the effect of any error regarding the measurement frequency is minimized since the rate of change of the transition cross section around that local minimum or maximum is at a minimum. Therefore, according to present method, the sample being measured can itself be used to calibrate the frequency at which absorption is measured. Thus, by calculating the density of the particular gas component to be measured at a local absorption minimum or maximum, an accurate value for the transition cross section of that gas component can be applied to the calculation of the density of that gas component in the gas sample.

The pathlength through the gas sample is the final variable relating to Beer's Law that must be accurately determined in order to calculate the density of a particular gas component in a gas vapor sample. The pathlength is the length of the laser path through the vapor. The pathlength can be accurately determined by one of ordinary skill in the art, thereby enabling this last variable to be accurately determined. An error in the pathlength represents a systematic error that can be corrected empirically.

In order for density measurements to be accurate, the light intensity emitted by the laser must be within the linear range of the detector. This can be achieved through the use of neutral density filters.

Techniques for enhancing the accuracy and the sensitivity of the diode laser vapor monitor are known in the art and include the use of signal averaging and double passing the light through the sample.

In addition to monitoring vapor density and composition, the vapor density monitor can be used to measure constituent distributions. Constituent distribution is a critical piece of data for determining a vaporization or deposition rate from the vapor density. The symmetry of the distribution can be determined qualitatively from the absorption waveform. For example, a skewed absorption waveform may indicate an uneven distribution.

Figure 2:
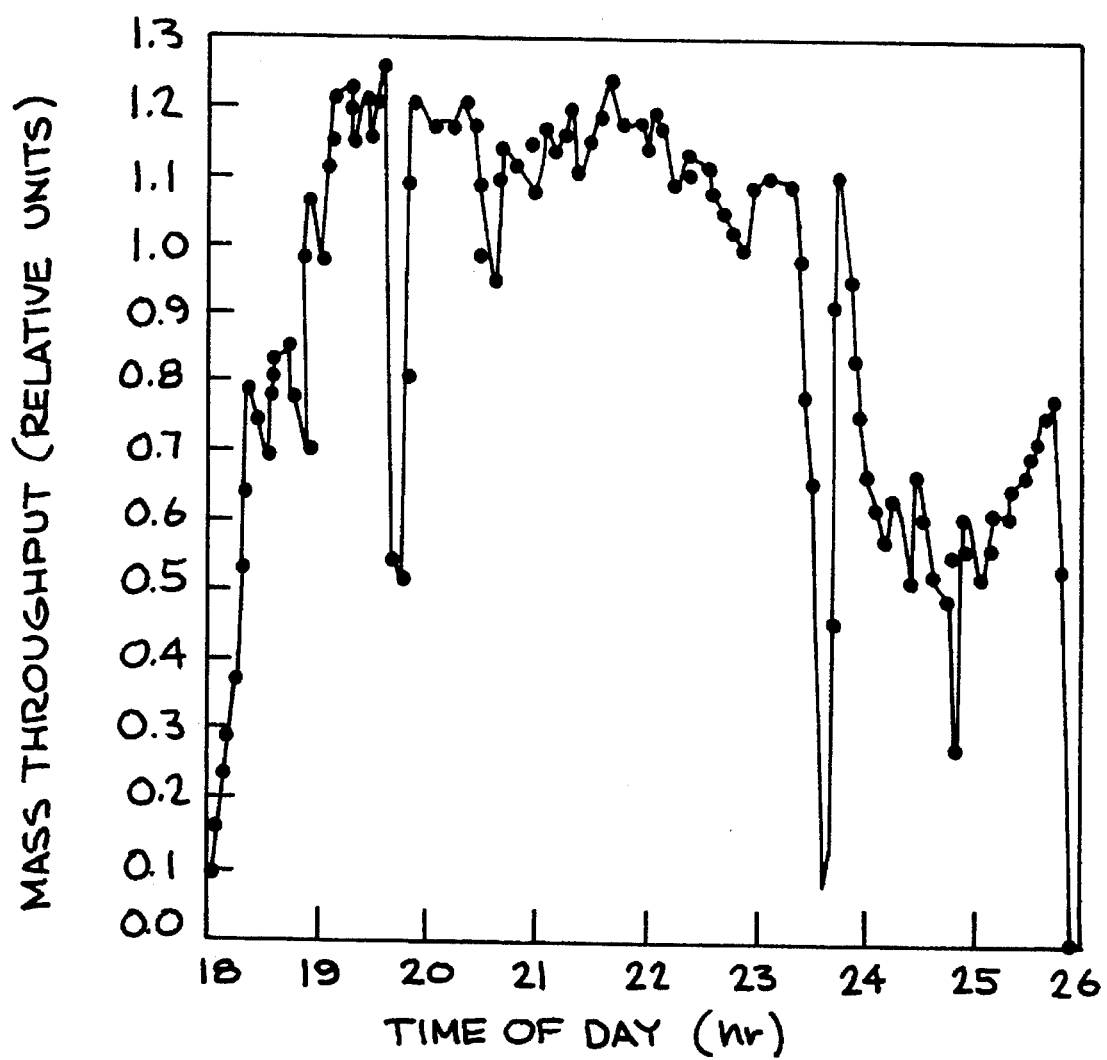
FIG. 2 shows that the accuracy of the vaporization rate monitor is better than 1% when compared to the post-run weight back to the amount of material vaporized.

Constituent distribution can be determined quantitatively when the form of the distribution is known. When operating with a spot source, it is common to express the density distribution as $$N(r,\theta) = (n_0/r^2) \cos^m \theta$$

where n is the density at radius r and angle theta from the normal to the pool, $n_0$ is a normalization constant representing the density at position $(r_0, \theta_0)$ and m is a number related to the efficiency of the vaporization. In low efficiency vaporization, m is taken to be 1 while m is taken to be 3 in high efficiency vaporization. With two distinct laser shots, the value of m can be measured for each component of the vapor. In addition, with the density distribution measured, the absorption waveform can then be used to calculate the velocity of the atoms in the vapor plume. Once the density distribution and the velocity are known, the flux distribution can be calculated. Knowledge of the flux distribution for each gas component allows the process to be optimized for both composition and deposition rate. As shown in FIG. 2, the accuracy of the vapor density monitor is shown to be better than 1% when compared post-run to the amount of material vaporized.

The present invention may be automated using computers. For example, tuning of the diode laser frequency to the specified absorption transition minimum or maximum can be accomplished by a lock-loop that employs an optogalvanic cell as an absorption standard. Scanning the laser in frequency acquires an absorption waveform. The waveform is then analyzed to determine the voltage offset necessary to keep the laser locked on the feature of interest.

Other software features of note include a method to analyze the Fabry-Perot data to obtain a frequency scale. Accurate determination of the frequency scale is critical for obtaining accurate data. In addition, the quality assurance features an error threshold as well as a warning threshold. Listed below are the checks done to insure data integrity.

1. Verify number of peaks in Fabry-Perot signal agree with default number;
2. Verify number of peaks found in Fabry-Perot signal agrees with number of Fabry-Perot peaks predicted by auto-correlation function;
3. Signal and reference signal levels within specified range;
4. Verify analysis program found half-height on way to determining baseline
5. Verify analysis program found enough points to make a baseline, but not too many;
6. Verify peak absorbance is significantly different than baseline;
7. Verify peak absorbance is significantly above the baseline noise;
8. Verify integrated absorption is a positive number;
9. Verify generation of a real internal temperature;
10. Verify electron beam was on during scan;
11. Verify have enough state densities to calculate internal temperature and total density;
12. Verify baseline noise is within acceptable limits;
13. Verify auto-correlation function on Fabry-Perot is in working condition.

Computers may also be used to provide continuous density data. The computer system measures the total absorption waveform at rates of up to 10 Hz and a continuous density signal is available between waveform scans. Thus, through the use of a personal computer, one is able to convert the absorbance data from the optical detector into density values in real-time. In the case of vaporization and deposition applications, one is able to continuously monitor and adjust vapor compositions.

In a further embodiment of the present invention, the diode laser vapor monitor can be made portable. In addition, laser light may be delivered across the gas sample from a remote site by means of optical fibers.

The vapor density monitor of the present invention enables a combination of desirable attributes that were not previously possible using direct deposition sensors, emission spectrometers, spectral lamp atomic absorption spectroscopy and ring-dye laser atomic absorption spectroscopy systems. Specifically, the present invention has demonstrated an absolute accuracy of 1%. The device of the present invention also has a high degree of spectral resolution thereby enabling one to distinguish between closely related species.

The present invention also provides a non-intrusive means for determining the density of a particular vapor component. As a result, the device of the present invention is able to continuously monitor gas samples without disrupting the flow of the gas sample. Further, the monitor of the present invention is more reliable and durable since there is no need to subject the sensor to the temperature extremes of the vapor.

The device of the present invention is also self-calibrating. There is no need to calibrate the detector since light absorbance is calculated based on the ratio of the light that passes through the vapor plume to the light split off from the beam prior to the vessel. Further, the light frequency of the laser need not be calibrated since the present method utilizes local minimums and maximums in the absorbance spectrum to insure that all measurements are performed at the appropriate frequency.

Finally, the present invention is significantly simpler, more durable and less expensive than the prior art devices, largely due to the use of a diode laser. The device of the present invention has the added advantage that it can be made portable, thereby enabling its use in a wide array of applications.

Figure 3:
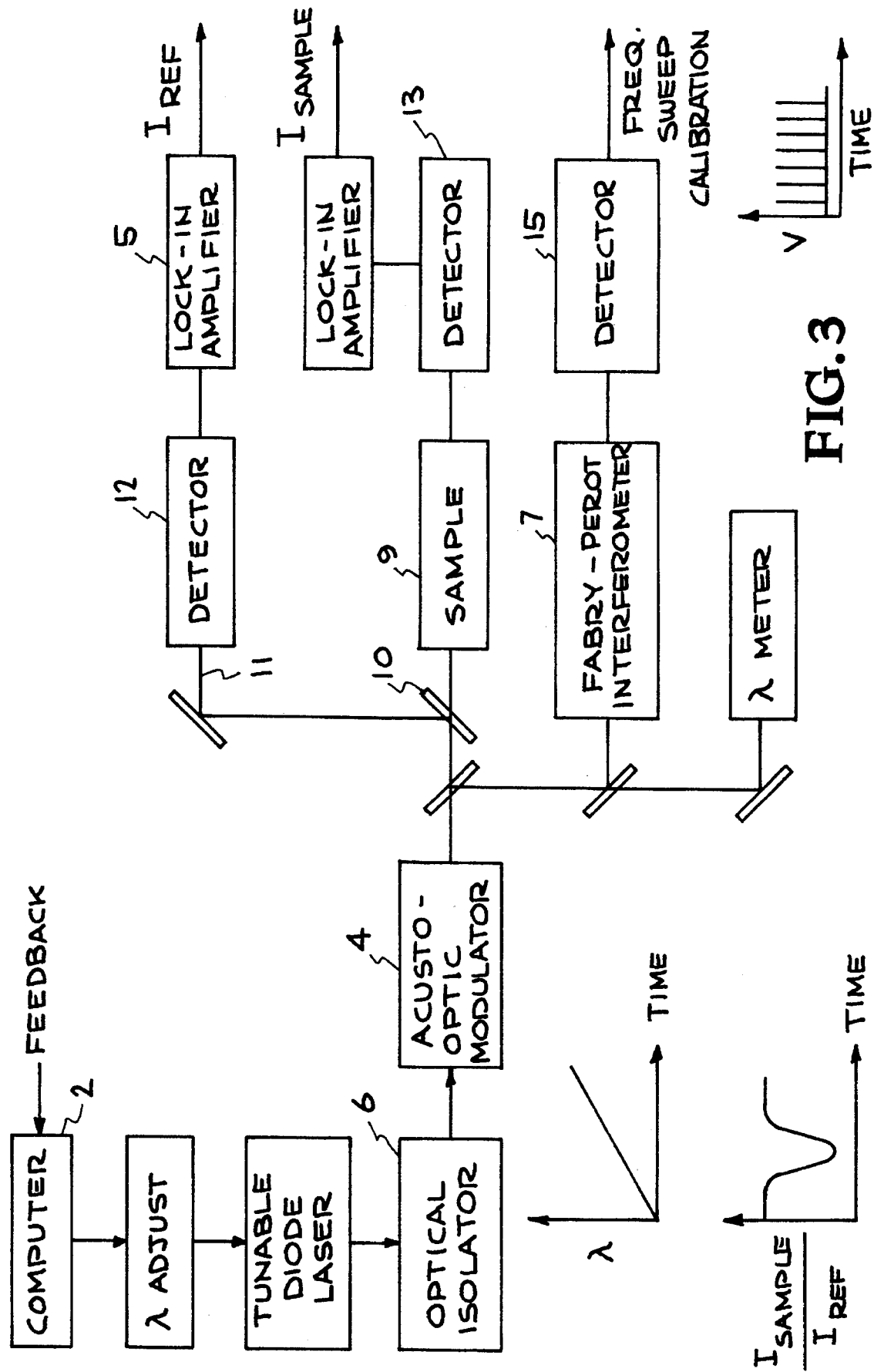
FIG. 3 provides a block diagram of the vapor density monitor of the present invention.

A block diagram of the vapor density monitor is presented in FIG. 3. The vapor density monitor comprises a tunable diode laser 1 which generates a light having an appropriate frequency and intensity. In the case of uranium processes, the diode laser is tuned to 6730 angstroms and preferably has an external cavity design. A preferred model is the commercially available New Focus model 6102. One facet of the semiconductor diode is coated with a high reflective coating and the other facet is coated with an anti-reflective coating. The diode-laser is placed in an external cavity where the laser cavity is defined by the high reflective coating and an external mirror. Tuning is achieved by modulation of the PCT piezo-electric transducer driven external mirror which changes the cavity length. This laser uses a high incidence angle Littman configuration grating to assure lasing in a single cavity mode. The external cavity provides significant advantages over previous systems where the frequency of a single-mode laser diode was modulated by tuning the current or temperature. By contrast to a temperature or current tuned single mode diode laser configuration, continuously tunable operation is achieved with the external cavity design. The external cavity design also provides great improvement in frequency stability.

In the system described, the sweep signal to scan the frequency of the diode laser is generated by the computer system 2 and is also used to synchronously trigger the digitizer 3 scan. The frequency modulated light from the swept diode laser 1 is then sinusoidally amplitude modulated by an acousto-optic 4 modulator. This amplitude modulation facilitates the use of a lock-in amplifier 5 for more sensitive signal detection and greater dynamic range. Acousto-optic modulation enables the demultiplexing of signals generated by other lasers monitoring other gas components at the same location, thereby enabling more than one gas component to be simultaneously monitored. An optical isolater 6 is required before the acousto-optic modulator to prevent optical feedback from entering the laser cavity. A Fabry-Perot interferometer 7 provides a scan width calibration. The laser is centered on the absorption transition to be monitored with a wavemeter and then held on the line with a correction signal generated by the computer from the absorption data.

The optical signal is then fiber 8 delivered to the remote vaporization vessel 9. Sending and receiving units have been designed that bolt directly to the vessel. The design of the sending unit includes an optical splitting means 10 required to split off a reference signal 11 before the light is sent through the vapor vessel. The reference signal is then sent to a first receiving unit 12 to measure the amount of light emitted by the laser. The reference signal 11 is used to detect and effectively cancel out noise generated by intensity fluctuations in the laser or optical delivery system. The absorption signal is detected by a second receiving unit 13 which consists of a lens and photo-opamp detector. Cables deliver the electrical signals back to the lock-in amplifier 5 and digitizer 3. The ratio of the signal to the reference can be graphically displayed 14. The density of the component being detected can be calculated based on the percentage of light transmitted, the pathlength and the atomic transition cross section. Detector 15 should actually be part of the Fabry-Perot. New Fabry-Perots models come with detector 15, older Wavemeter 16 models do not.

Figure 4:
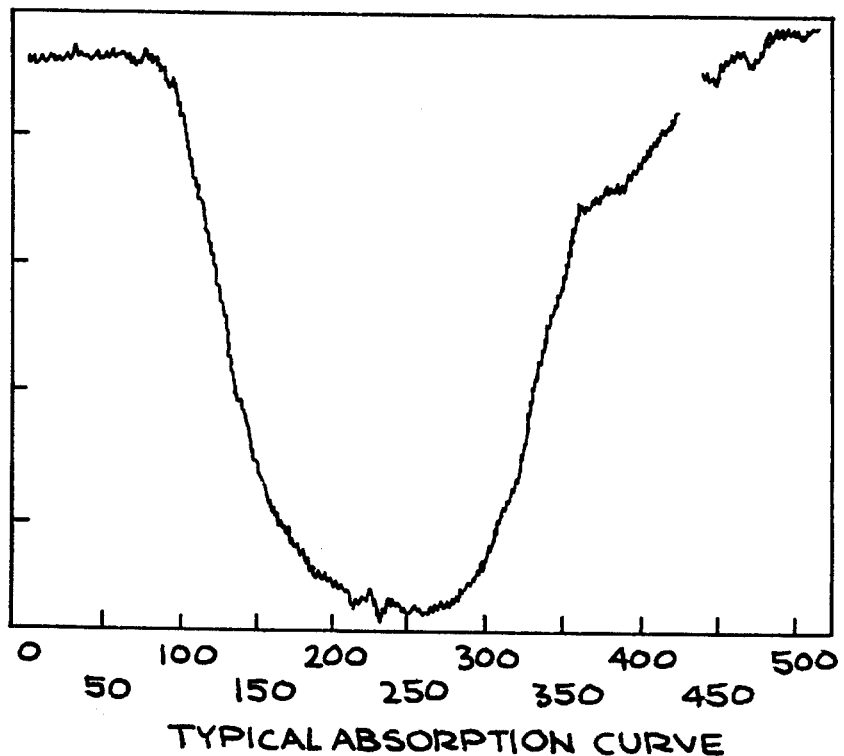
FIG. 4 depicts the digitized ratio of the light transmitted through the sample to the light transmitted by the reference source.
Figure 5:
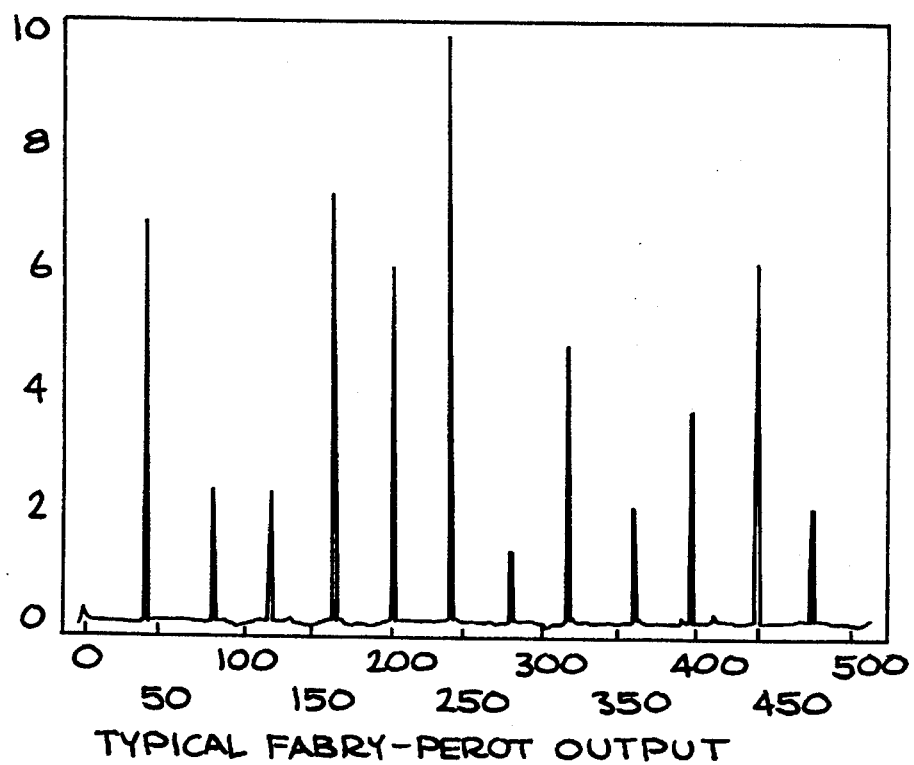
FIG. 5 depicts the corresponding digitized 300 MHz Fabry-Perot signal with a 4 GHz sweep width.
Figure 6:
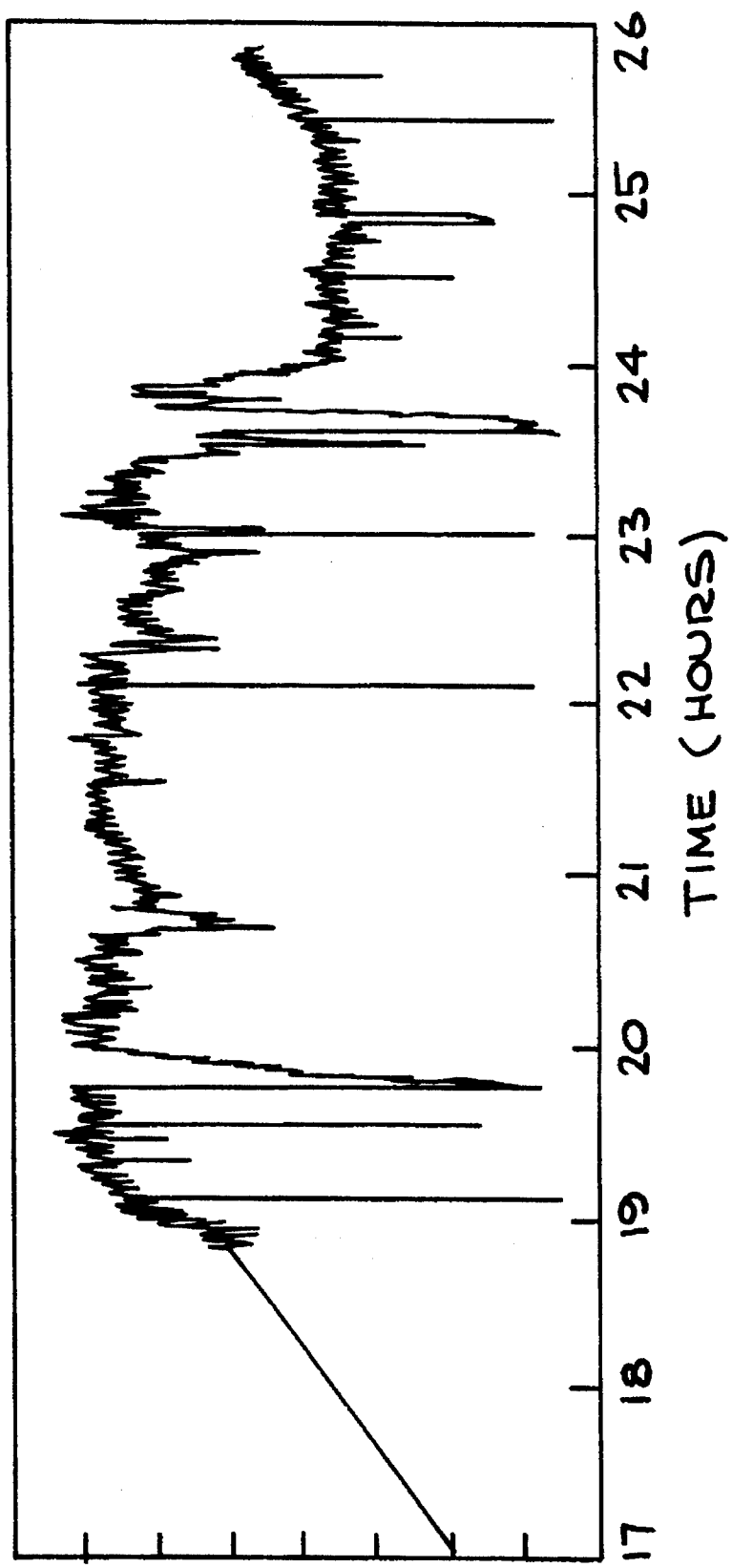
FIG. 6 compares the calculated uranium densities based on 5695° A and 6730° A ground state transitions.

FIG. 2 depicts the raw data generated by the vapor density monitor. The diode laser is scanned through the entire Doppler broadened transition. The digitized ratio of the light transmitted through the sample to the light transmitted by the reference source is shown in FIG. 4. A computer may be used to calculate the absorption signal depicted in FIG. 4. See attached Appendix. The corresponding digitized 300 MHz Fabry-Perot signal with a 4 GHz sweep width is depicted in FIG. 5.

An integration of the waveform generated after the logarithm is calculated is then performed. This scalar quantity is converted into a line integrated density by dividing the scalar quantity by the pathlength and the transition cross section for that frequency. Although not used to calculate density, the Doppler broadened absorption line shape can provide information regarding the spatial distribution of the vapor plume.

In order to determine the accuracy of the vapor density monitor, a weigh-back calibration test was performed. The uranium vapor passing through the diagnostic location was condensed and collected. The amount of uranium collected was then weighed and compared against what was predicted by the vapor density monitor. As shown in FIG. 2, the vapor density monitor's calculation of 721 mass units was in close agreement with the 715 mass units actually measured.

4. Monitoring Changes In Vapor Density Composition In Real Time

The vapor density monitor has the particular ability of continuously monitoring changes in vapor densities in real time. FIG. 7 shows the change in iron and uranium vapor density observed when a charge of iron is introduced into a pool of molten iron-uranium alloy. As shown in FIG. 7, the iron vaporization rate increases while the uranium vaporization rate decreases. Then, once most of the iron charge has been vaporized, the vapor composition relaxes to an iron density that is somewhat higher than before the charge was introduced. Thus, the vapor density monitor has been shown to indicate changes in vapor density and composition in real time.

5. Monitoring Of Titanium Alloy Melt Rates Using The Diode Laser Vapor Monitor

Commercial production melt rates for titanium alloys are in the range of 400 kg/hr. During the melting process, vapor losses of 2–3% are typical with the vapor composition being roughly 50% titanium, 50% aluminum and less than 1% vanadium. At this vaporization rate, the vapor velocity is approximately 1000 m/s and the vapor source temperature is approximately 2200° K. Under these conditions 5 kg/hr of titanium, 5 kg/hr of aluminum and 0.1 kg/hr of vanadium are vaporized.

These vaporization rates can be measured spectroscopically. Titanium vapor densities may be measured at 3348.54°. Aluminum vapor densities may be measured at 3444.86°. Vanadium vapor densities may be measured at 4832.42°. Therefore, by monitoring the absorption at these three wavelengths, it is possible to monitor the composition of the titanium alloy being formed.

While the invention of this patent application is disclosed by reference to the aforementioned examples, it is to be understood that these examples are intended in an illustrative rather than limiting sense, as it is contemplated that modifications will readily occur to those skilled in the art, within the spirit of the invention and the scope of the appended claims.

What is claimed is:

1. A method for determining the density of a component of a gas vapor using a tunable laser, said component absorbing light at an expected maximum absorptance frequency, comprising the steps of:

self-tuning the tunable laser to transmit a laser source beam at a local maximum absorptance frequency of the component by
    transmitting a laser source beam through a first path of at least one predetermined paths through the gas vapor,
    sweeping the frequency of the laser source beam through a frequency range including said expected maximum absorptance frequency, and
    during the step of sweeping the frequency of the laser source beam,
    measuring the intensity of the transmitted laser source beam after having been transmitted through the first path of at least one predetermined path through the gas vapor to determine the frequency at which the gas vapor exhibits a maximum absorptance; and
    locking the laser source beam frequency at the frequency at which the gas vapor exhibits a maximum absorptance frequency;
  measuring the intensity of said locked-frequency laser source beam;
  transmitting said locked-frequency laser source beam through a least one of said predetermined paths through the gas vapor;
  measuring the intensity of the transmitted locked-frequency laser source beam after having been transmitted through said at least one of said predetermined paths through the gas vapor; and
  calculating the density of the component in said at least one of said predetermined paths using Beer's law.

2. The method as recited in claim 1 wherein said step of self-tuning the tunable laser to transmit a laser source beam at a local maximum absorptance frequency of the component is periodically repeated to assure that the laser source beam frequency remains locked onto the local maximum absorptance frequency.

* * * * *